(12) United States Patent
Zettel et al.

(10) Patent No.: US 7,369,695 B2
(45) Date of Patent: May 6, 2008

(54) METHOD AND APPARATUS FOR METAL ARTIFACT REDUCTION IN 3D X-RAY IMAGE RECONSTRUCTION USING ARTIFACT SPATIAL INFORMATION

(75) Inventors: Hubert A. Zettel, Waukesha, WI (US); Daniel E. Groszmann, Cambridge, MA (US); Tina Kapur, Bellevue, WA (US)

(73) Assignee: General Electric Company, Schenectady, NY (US)

( * ) Notice: Subject to any disclaimer, the term of this patent is extended or adjusted under 35 U.S.C. 154(b) by 662 days.

(21) Appl. No.: 10/922,765

(22) Filed: Aug. 20, 2004

(65) Prior Publication Data
US 2006/0039591 A1 Feb. 23, 2006

(51) Int. Cl.
*G06K 9/00* (2006.01)
(52) U.S. Cl. ............................. 382/132; 382/154; 378/4
(58) Field of Classification Search ................ 382/100, 382/128, 129, 130, 131, 132, 154, 156, 168, 382/181, 194, 199, 203, 216, 232, 243, 255, 382/260, 274–277, 285, 305, 106, 133; 600/425, 600/426; 378/4, 8, 43, 62
See application file for complete search history.

(56) References Cited

U.S. PATENT DOCUMENTS 6,118,845 A * 9/2000 Simon et al. ................. 378/62
6,470,207 B1 * 10/2002 Simon et al. ................ 600/426
6,483,892 B1 * 11/2002 Wang et al. ................... 378/43
6,549,607 B1 * 4/2003 Webber .......................... 378/8
6,801,594 B1 * 10/2004 Ali et al. ........................ 378/4
6,845,142 B2 * 1/2005 Ohishi ............................ 378/8
6,990,368 B2 * 1/2006 Simon et al. ................ 600/425

FOREIGN PATENT DOCUMENTS

WO WO 2004/017263 A2 2/2004

OTHER PUBLICATIONS

European Search Report for Application No. 05254709, dated Aug. 12, 2005.

* cited by examiner

*Primary Examiner*—Seyed Azarian
(74) *Attorney, Agent, or Firm*—McAndrews, Held & Malloy, Ltd.; Peter J. Vogel; Michael A. Dellapenna

(57) ABSTRACT

The present invention relates to a method and apparatus for reducing metal artifact in image reconstruction. In at least one embodiment, the method for reducing metal artifacts in image reconstruction comprises collecting at least one uncalibrated image (an X-ray or fluoroscopic image for example) and calibrating the at least one uncalibrated image, forming at least one calibrated fluoroscopic image. A patient to transmitter transform is computed using at least the at least one calibrated image. A reconstructed volume is formed using at least a patient to transmitter transform. At least two of the at least one calibrated fluoroscopic image, the patient to transmitter transform and the reconstructed volume may be combined, forming at least one display image. This image may then be displayed, using a display device for example.

18 Claims, 4 Drawing Sheets

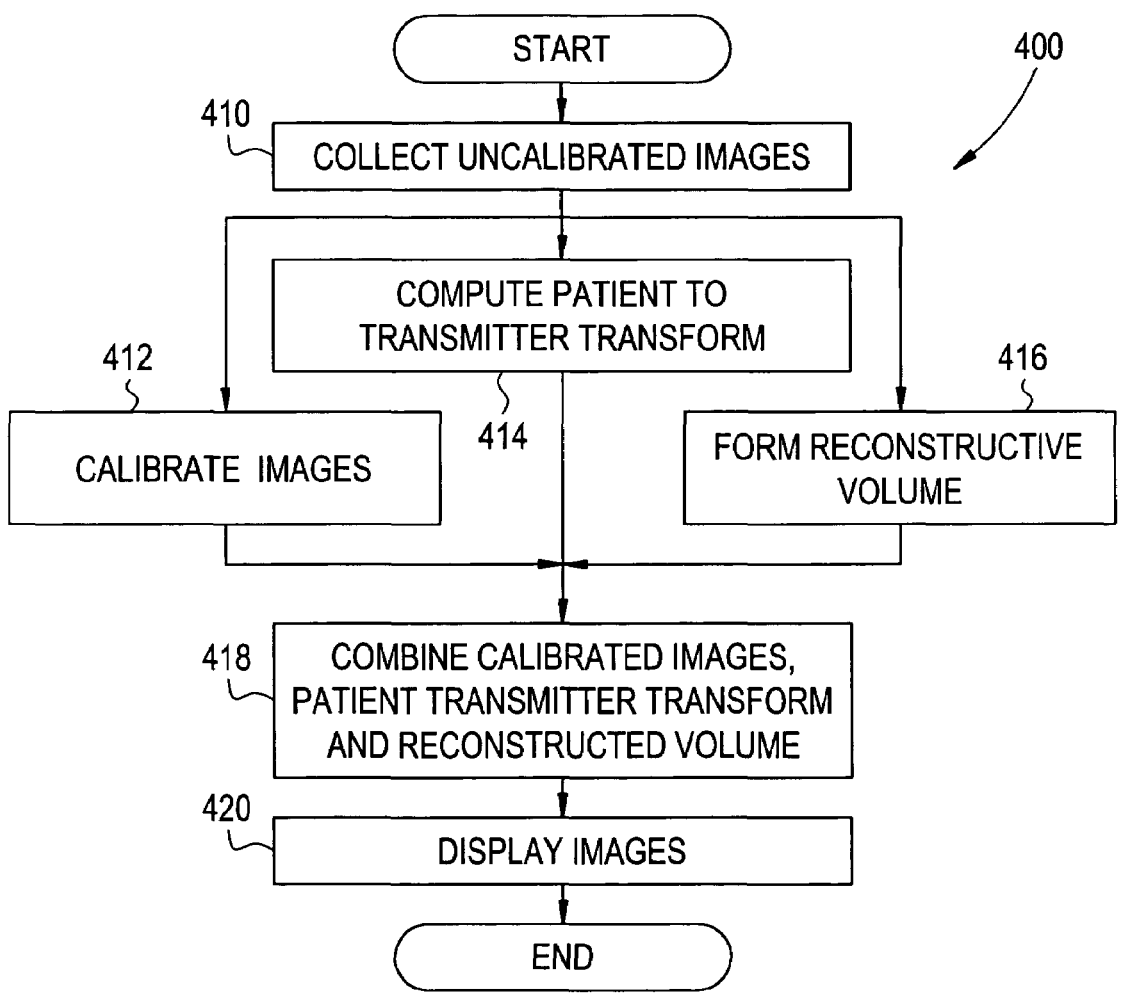

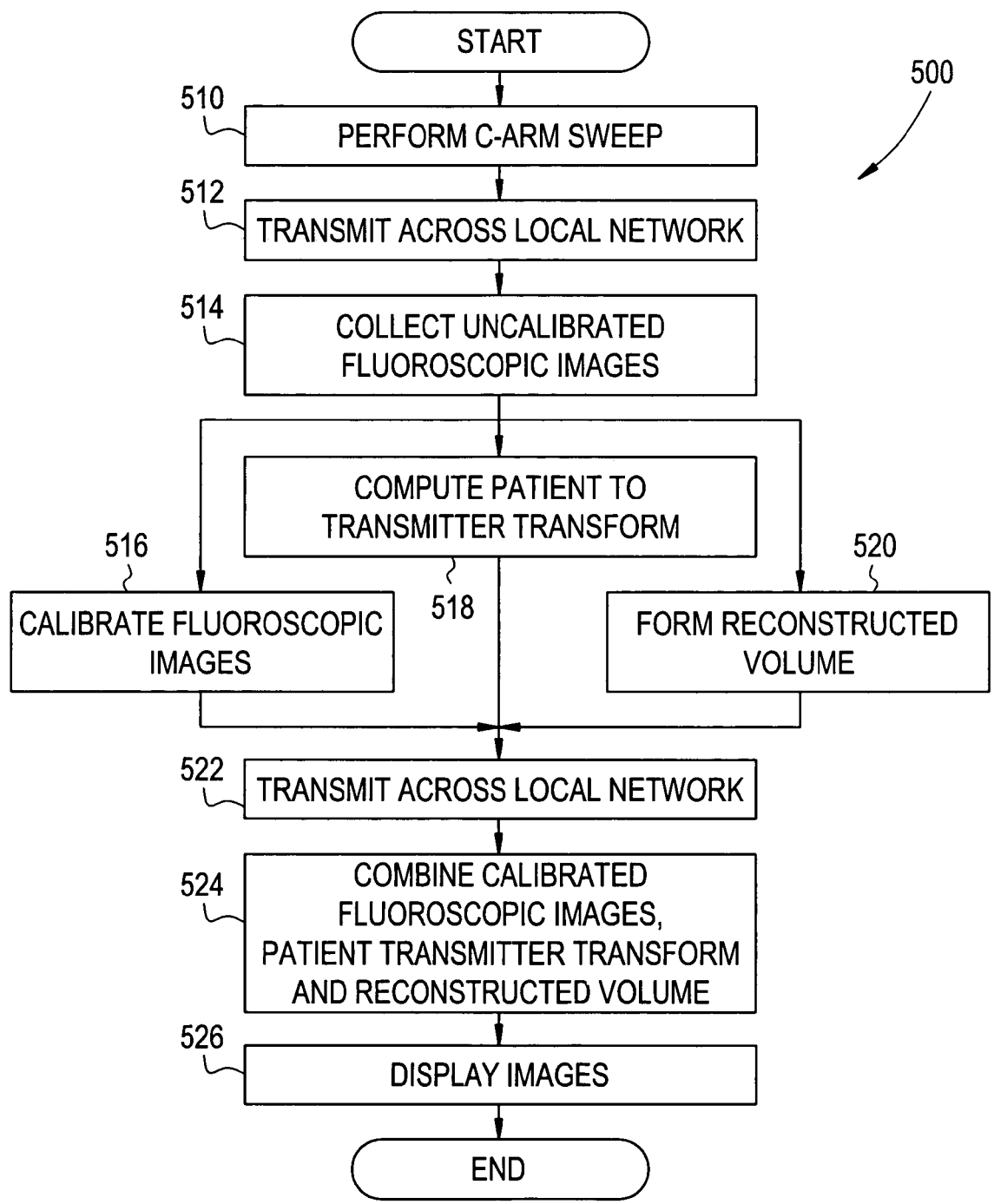

METHOD AND APPARATUS FOR METAL ARTIFACT REDUCTION IN 3D X-RAY IMAGE RECONSTRUCTION USING ARTIFACT SPATIAL INFORMATION

RELATED APPLICATIONS

[Not Applicable]

FEDERALLY SPONSORED RESEARCH OR DEVELOPMENT

[Not Applicable]

MICROFICEH/COPYRIGHT REFERENCE

[Not Applicable]

BACKGROUND OF THE INVENTION

This application is directed in general to image reconstruction. More particularly, this application is directed to metal artifact reduction in an image reconstruction using artifact spatial information.

Forming CT and 3D Fluoroscopic images of a patient's anatomy is well known in the art. It should be appreciated that it is desirable for surgeons to see how well internal fixation of metal implants was performed in post surgical images. However, it is known that metal implants such as pedicle screws and fracture plates/pins for example, may generate streak artifacts in the formation of such fluoroscopic images. Such streak artifacts are created due to the sharp difference in signal attenuation at the boundary of the metal implants and the patient's anatomy.

Many techniques or methods are known for reducing, alternating or eliminating such artifact streaks. One known technique for reducing artifact streaks includes applying ramp filters during the reconstruction of the scan data. Such ramp filters may mitigate but do not eliminate the streak artifacts, since the filters are generally broadly applied to the entire scan data set. Being able to view the surgery site with minimal metal-related steak artifacts is highly desirable.

BRIEF SUMMARY OF THE INVENTION

One embodiment of the present invention relates to an image reconstruction device, system or machine. More particularly, one embodiment relates to a 3D X-ray image reconstruction method and apparatus that reduces or minimizes metal-related streak artifacts.

One embodiment of the present invention relates to a method for conducting image reconstruction (X-ray or fluoroscopic image reconstruction for example). In at least one embodiment the method comprises collecting at least one uncalibrated image (an uncalibrated X-ray or fluoroscopic image for example). The method further comprises calibrating the at least one uncalibrated image, forming at least one calibrated image. In at least one embodiment, the method comprises locating at least one artifact. It is also contemplates that, in at least one embodiment, at least one image is displayed.

In at least one embodiment, the method for conducting image reconstruction may comprise computing patient to transmitter transform, where the patient to transmitter transform may be computed using at least the at least one uncalibrated image. Further, the patient to transmitter transform may be used to form a reconstructed volume, where the reconstructed volume may be formed using at least the at least one uncalibrated image. It is further contemplated that the method comprises combining at least two of the at least one calibrated image, the patient to transmitter transform and the reconstructed volume.

Still another embodiment relates to a method for reducing metal artifacts in 3D X-ray reconstruction. This embodiment comprises collecting at least one uncalibrated image (an X-ray or fluoroscopic image for example) and calibrating the at least one uncalibrated image, forming at least one calibrated image (a calibrated X-ray or fluoroscopic image for example). A patient to transmitter transform is computed using at least the at least one calibrated image. A reconstructed volume is formed using at least the patient to transmitter transform. At least two of the at least one calibrated fluoroscopic image, the patient to transmitter transform and the reconstructed volume are combined, forming at least one display image. This image may then be displayed, using a display device for example.

In at least one or more embodiments, the at least one uncalibrated image comprises at least one uncalibrated fluoroscopic image and the at least one calibrated image comprise at least one calibrated fluoroscopic image. In at least one embodiment, calibrating the at least one uncalibrated image comprises performing at least one C-arm sweep, locating at least one artifact and/or removing at least one calibration marker. Embodiments further comprise transmitting the at least one uncalibrated fluoroscopic image across at least one local network.

Still other embodiments for reducing metal artifacts in 3D X-ray reconstruction comprise forming the reconstructed volume by rotating at least one fluoroscopic image, undoing any C-arm settings. An intensity of the at least one rotated fluoroscopic image is inverted and filtered for apriori spatially known metal artifacts. At least one of the filtered fluoroscopic images is back projected forming the reconstructed volume.

One other embodiment of the present invention relates to an apparatus for reducing metal artifacts in image reconstruction (X-ray image reconstruction for example), comprising a module adapted to collect at least one uncalibrated image and a module adapted to calibrate the at least one uncalibrated image, forming at least one calibrated image. The apparatus further comprises a display device adapted to display at least one image having reduced metal artifacts.

BRIEF DESCRIPTION OF SEVERAL VIEWS OF THE DRAWINGS

FIG. 4 illustrates a high-level flow diagram depicting a method for performing image reconstruction with reduced metal-related streak artifacts in image reconstruction apparatus (similar to that illustrated in FIGS. 1, 2, and 3) using artifact spatial information with certain embodiments of the present invention.

FIG. 5 illustrates a detailed flow diagram depicting yet another method for performing for image reconstructing with reduced metal-related streak artifacts using an image reconstruction apparatus (similar to that illustrated in FIGS. 1, 2 and 3) using artifact spatial information with certain embodiments of the present invention.

Figure 1:
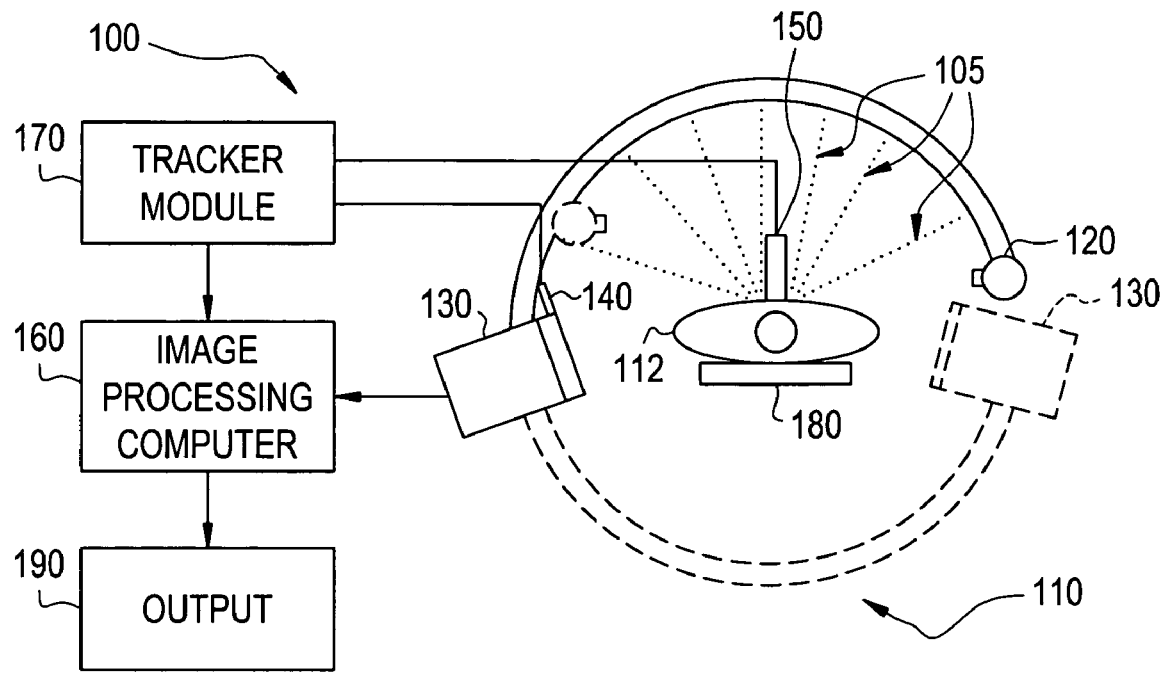
FIG. 1 illustrates an image reconstruction system used in accordance with a certain embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

For the purpose of illustration only, the following detailed description references a certain embodiments of an X-ray or fluoroscopic image apparatus, system, device or machine. However, it is understood that the present invention may be used with other devices or imaging systems.

3D fluoroscopic images may be generated from 2D fluoroscopic projection images by the image device or system illustrated in FIGS. 1, 2 and 3, using cone beam reconstruction techniques similar to those discussed below. The inherent position and/or orientation information for each 2D projection taken or acquired by the C-arm helps ensure the spatial relationship between the plurality of 2D projection images used to create 3D images. Since the tracking information is, in at least one embodiment, dynamically referenced to the 2D images, embodiments are enabled to directly locate one or more metal implants in each of the 2D images. In one embodiment, a pointer may be used to identify the location of the one or more implants on or in the patient. The pointer may be used to collect various points to outline the volume of the one or more implants.

In another embodiment, a pointer may be used to trace the one or more implants on at least one of the 2D fluoroscopic images and, then given the coordinates of the traced outline of the one or more implants, translate those coordinates to the other 2D images. Still another embodiment comprises using standard CAD model information for the implant and use the pointer to correlate the implant CAD model position to its placement in each of the 2D views. Once the implant is located, one or more filtering, averaging or smoothing techniques may be applied to eliminate the streak artifacts caused during the reconstruction, while preserving the necessary information regarding the implant location.

One or more embodiments of the present invention eliminates metal-related streak artifacts that degrade image quality. One or more embodiments provide a differentiating feature on X-ray systems that perform 3D fluoroscopic reconstructions, especially in spine and orthopedics applications.

Previous attempts at reducing metal-related artifacts were performed without prior knowledge of the metal that was present or used in the patient. In the case of CT, images are created from a specific volume without knowing the position and orientation of the metal within the patient. In the case where specific position and orientation information of the metal object within the patient is available and directly correlated to the generated 2D images collected to create the 3D data set, this specific knowledge may be used to provide localized image processing to minimize or eliminate streak artifacts during the image processing, cone beam reconstruction process for example.

FIG. 1 illustrates an imaging device, machine, system or apparatus, generally designated 100, used in accordance with embodiments of the present invention. It is contemplated that system 100 may comprise a variety of systems including an X-ray system, a CT system, an EBT system, an ultrasound system, an MR system, or other imaging system.

In at least one embodiment, system 100 includes a C-arm 110, one or more X-ray sources 120, one or more X-ray detectors 130, one or more electromagnetic (EM) sensors 140, an EM transmitter 150, an image processor 160, a tracker module 170, a positioning device 180 and an output 190. In the illustrated embodiment, tracker module 170 is depicted communicating with at least EM sensor 140, EM transmitter 150, and image processor 160. FIG. 1 further illustrates image processor 160 communicating with at least X-ray detector 130, tracker module 170 and output 190.

In at least one embodiment, X-ray source 120 and X-ray detector 130 are mounted on opposing sides of the C-arm 110. The X-ray source 120 and X-ray detector 130 may be movably mounted on the C-arm 110. In one embodiment, EM sensor 140 is mounted on X-ray detector 130. The EM transmitter 150 is positioned on an object 112, such as a patient, to be imaged. Alternatively, EM transmitter 150 may be located on the X-ray detector 130, and EM sensor 140 may be located on an object or patient 112 being imaged. The object or patient 112 is positioned on or in positioning device 180. In at least one embodiment, positioning device 180 comprises a table, a table bucky, a vertical bucky, a support or other positioning device adapted to be used.

In at least one embodiment, C-arm 110 is movable in several directions along multiple image acquisition paths, including, for example, an orbital direction, a longitudinal direction, a lateral direction, a transverse direction, a pivotal direction and a "wig-wag" direction. In at least one embodiment, X-ray source 120 and detector 130 are movably positioned on C-arm 110. Thus, the C-arm 110, along with X-ray source 120 and X-ray detector 130, may be moved and positioned about the positioning device 180 on or in which object 112 has been situated. The C-arm 110 is used to position the X-ray source 120 and detector 130 about object 112 so that one or more X-rays 105 (or other energy) may irradiate object 112 for use in producing one or more images. The C-arm 110 may be moved or re-positioned at a variety of scan angles around object 112, obtaining a plurality of images. As the C-arm 110 moves, the distance between the X-ray detector 130 and the object 112 may vary. Further, the distance between X-ray source 120 and object 112 may also vary.

It is contemplated that, in at least one embodiment, the X-ray source 120 and detector 130 on C-arm 110 may move in a cross-arm or orbital motion, for example. In an orbital motion, the X-ray source 120 and the detector 130 do not move in a circular path. In tomographic image reconstruction using orbital motion, a distance between detector 130 and object 112 (and a distance between source 120 and object 112) may vary during collection of projection images.

In at least one embodiment, a position of the X-ray detector 130 may be recorded for one or more projection images. Additionally, a distance between detector 130 and the X-ray source 120 may be determined. A magnification change may be quantified and compensated for during tomographic image reconstruction using detector 130 position and detector-to-object distance. The EM sensor 140 or other tracking device may be placed on detector 130. The EM transmitter 150 or other tracking device may be placed on the object 112. Data from the sensor 140 and transmitter 150 may be used to determine a position of detector 130 during a trajectory of detector 130. Other tracking devices, such as optical or mechanical tracking devices, may be used to determine a position of one or more components in the system 100.

In at least one embodiment, transmitter 150 broadcasts a signal, such as a magnetic field, that is detected by sensor 140. The tracker module 170 may use data from the transmitter 150 to determine a position of the detector 130 with respect to object 112. Differences in position and, thus, distance between the detector 130 and the object 112 may correspond to differences in magnification in obtained X-ray projection images.

It is contemplated that changing the distance between detector 130 and object 112 and/or the distance between the source 120 and object 112 changes the magnification of the object 112 projected onto the detector for point sources or near-point sources that emit non-parallel beams, such as X-rays. If the field of view of the X-ray source 120 is constant, as object 112 approaches the X-ray source 120, the object 112 occupies more of the field of view and therefore projects as a larger image onto the detector 130. In an embodiment, the detector-to-object distance is varied to maintain the object 112 at a virtual isocenter of the system 100. In an embodiment, C-arm 110, source 120 and/or detector 130 on the C-arm 110 may be moved in any plane or not moved to position object 112 at the virtual isocenter in the field of view of the detector 130. Measuring the varying detector-to-object and/or source-to-object distance enables the image processor 160 to compensate for the change in distance and thus the change in magnification. The tracker module 170 may use data from the EM sensor 140 and EM transmitter 150 or other tracking device to track the detector-to-object distance.

Alternatively, EM sensor 140 or EM transmitter 150 may be mounted on the source 120 with the EM transmitter 150 or EM sensor 140 on the object 112 to determine position of the source 120. A position of the X-ray source 120 may be recorded and used with the source-to-detector distance to determine and account for the magnification change. Tracker module 170 may monitor a position of an instrument or tool used during a diagnostic or surgical procedure, for example.

The tracker module 170 monitors a position of object 112, X-ray detector 130, and/or X-ray source 120 in the system 100. The tracker module 170 may provide position data in a reference coordinate system with respect to object 112, source 120, and/or detector 130. The image processor 160 uses the position data when processing the image data to reconstruct 2D and/or 3D images. The position data may also be used for other purposes, such as surgical navigation, for example. In one embodiment, the tracker module 170 continuously calculates the positions of the X-ray detector 130 and object 112 with respect to a coordinate system defined relative to a coordinate system reference point or central axis. In at least one embodiment, the image processor 160 generates control or trigger commands to the X-ray source 120 or source controller to scan the object 112 based on position data.

In at least one embodiment, the image processor 160 collects a series of image exposures from the detector 130 as the C-arm 110 is moved. The detector 130 receives an image exposure each time the X-ray source 120 is triggered. The image processor 160 combines one or more image exposures with reference data, reconstructing a 3D volumetric data set for example. The 3D volumetric data set may be used to generate images, such as slices, or a region of interest from the object 112. For example, the image processor 160 may produce sagittal, coronal, and/or axial views of a patient spine, knee, or other area using 3D volumetric data set. The image processor 160 may be implemented in software and/or hardware, where the image processor 160 may comprise a general purpose computer, a microprocessor, a microcontroller and/or an application-specific integrated circuit, for example.

In one or more embodiments, 3D image reconstruction may be formed by combining successive slices or planes of scanned object 112 using a fan beam for example. A 3D image reconstruction may also be formed by rotating source 120 and detector 130 around object 112 to obtain cone or area beam projections of object 112. In a cone beam projection, the object 112 may be illuminated with a point source and X-ray flux measured on a plane by the detector 130. The distance from object 112 to the detector 130 and the distance from object 112 to the source 120 may be used to determine parallel projections for image reconstruction. It is also contemplated that filtered backprojection may also be used to reconstruct a 3D image based on filtering and backprojecting a plane in a cone beam. In a filtered backprojection, individual fan beam or cone beam projections are analyzed and combined to form a 3D reconstruction image. Fan beams are tilted out of a source-detector plane of rotation for analysis in a new coordinate system for filtered backprojection. Projection data is weighted based on distance and convolved. Then, the convolved weighted projections are backprojected over a 3D reconstruction grid to reconstruct a 3D image.

After one or more image(s) have been reconstructed, the image processor 160 may transmit the image(s) to the output 190. It is contemplated that output 190 may comprise a display, a printer, facsimile, electronic mail, a storage unit, or other medium, for example. It is further contemplated that, in at least one embodiment, output 190 may comprise a laptop, a PDA, cell phone or other wireless device communicating wirelessly with image processing computer 160. The image(s) may be displayed and/or stored via the output 190 for use by a user such as a technician, physician, surgeon, other healthcare practitioner, or security officer.

In operation, for example, a patient's mid-spinal area may be scanned in the system 100. The C-arm 110 may not reach all positions of a mid-spinal scan when the patient is positioned on a table, such as the positioner 180. Therefore, the C-arm 110 may be moved and positioned from a side. As the C-arm 110 is moved in a non-circular motion, the spine may not remain centered in scanned images because the path of the C-arm 110 may not be circular. The C-arm 110 may be moved, such as by raising and lowering the C-arm 110 on a C-arm support, to keep the spine in the center (e.g., a virtual isocenter).

As the C-arm 110 is moved and the spine is not moved, the spine is located closer or farther from X-ray source 120. Thus, obtained images have a different magnification from start to finish (for example, five vertebral levels in a first image to three vertebral levels in a last image due to more magnification) because the C-arm 110 moves in a non-circular arc. A change in magnification may be determined because the position of the detector 130 with respect to the object being scanned is measured or determined by the tracker module 170 using the EM transmitter 150 and sensor 140, for example. Then, the magnification change is taken into account during reconstruction of a 3D volume image of the mid-spinal area. Rather than using a fixed distance in standard image reconstruction algorithms, the variable distance values are used in reconstruction calculations for the image(s).

Figure 2:
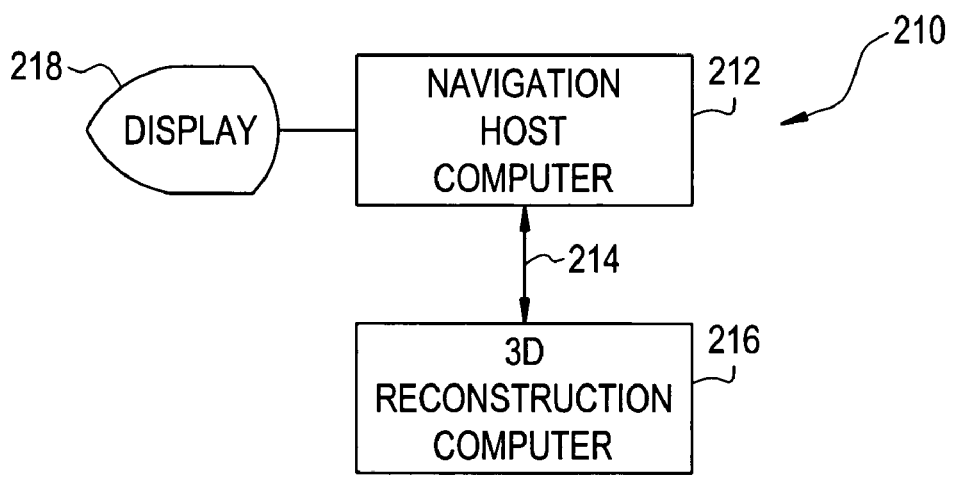
FIG. 2 illustrates a high level block diagram of an image reconstruction device, machine, system or apparatus in accordance with certain embodiments of the present invention.

FIG. 2 depicts a high level block diagram of an image reconstruction device, system, machine or apparatus, 210 for creating a 3D volume in accordance with embodiments of the present invention. In the illustrated embodiment, apparatus 210 comprises at least one navigation host computer 212 and at least one 3D construction computer 216 communicating via one or more local networks 214. In at least one embodiment of the present invention, at least one or more displays 218 are illustrated communicating with the navigational host computer 212.

In one embodiment, image reconstruction device 210 is part of imaging system 100 illustrated in FIG. 1. In this embodiment, output 190 comprises display 218, while image processor 160 comprises navigation host computer 212, 3D reconstruction computer 216 and network 214. In another embodiment, image reconstruction device 210 and image system 100 are separate devices that communicate.

Figure 3:
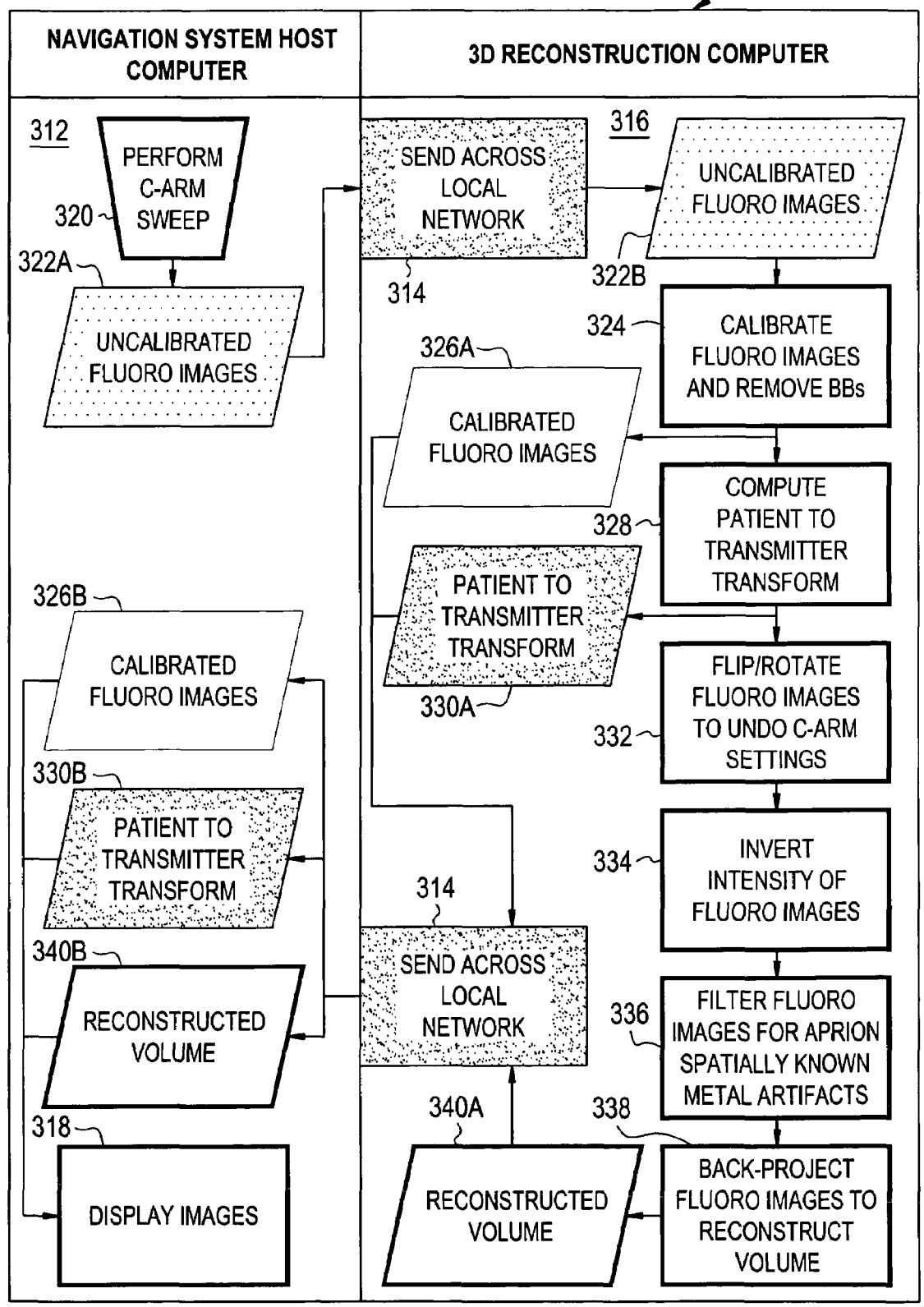
FIG. 3 illustrates a detailed block diagram of an image reconstruction device, machine, system or apparatus (similar to that illustrated in FIG. 2) for reducing or eliminating metal-related streak artifacts using artifact spatial information with certain embodiments of the present invention.

FIG. 3 depicts a more detailed block diagram of an image reconstruction device, system, machine or apparatus for creating 3D volume in accordance with at least one embodiment of the present invention. In this illustrated embodiment, system or apparatus generally designated 300, comprises at least one navigation system host computer 312 communicating with at least a 3D reconstruction computer 316 via one or more local networks 314. In the illustrated embodiment, the navigation system host computer 312 performs at least one C-arm sweep 320 of a patient for example. One or more uncalibrated images 322A (uncalibrated X-ray or fluoroscopic images for example) are generated from the one or more C-arm sweeps 320. The navigation system host computer 312 transmits the one or more uncalibrated images 322A to the 3D reconstruction computer across the local area network 314.

In at least one embodiment, the 3D reconstruction computer 316 receives the one or more uncalibrated images 312B. In this embodiment, the 3D reconstruction computer 116 calibrates the images, removing one or more radiopaque or calibration markers (ball bearings ("BB's") for example), forming one or more calibrated images 326A (calibrated X-ray or fluoroscopic images for example). The 3D reconstruction computer 316 further takes the one or more calibrated images and computes a patient transmitter transform, forming the patient transmitter transform 330A.

In at least one embodiment 3D reconstruction computer 316 receives the one or more patient to transmitter transforms, flipping or rotating the images to undo the C-arm settings 332. Method 300 further comprises flipping the rotated images inverting the intensity 334. The fluoroscopic images are filtered, using one or more filters, forming apriori spacing known metal artifacts 336. The filtered fluoroscopic images are then back projected to reconstruct the volume, forming reconstructed volume 340A.

In at least one embodiment, 3D reconstruction computer 316 transmits the one or more collaborated images 326A, patient to transmitter transform 330A and the reconstructed volume 340A to the navigation system host computer 312, via one or more local networks 314. The navigation system host computer 312, receives the calibrated images 326B, the patient to transmitter transforms 330B and the reconstructed volume 340B, forming one or more images for display. The images are displayed on a display device 218 or output 190.

FIG. 4 depicts a high level flow diagram depicting one method, generally designated 400, for creating a 3D volume in accordance with at least one embodiment of the present invention. In at least one embodiment, method 400 comprises block 410, collecting one or more images (uncalibrated X-ray or fluoroscopic images for example).

Method 400 further comprises block 414, calibrating one or more of images (calibrated X-ray or fluoroscopic image for example); block 416, computing patient to transmitter transform; and block 418, forming reconstructed volume. In at least one embodiment, block 418 may comprise combining the callibrated images, the patient transmitter transform and reconstructed volume. Method 400 further comprises block 420, displaying one or more images.

FIG. 5 depicts a detailed flow diagram depicting a method, generally designated 500, for creating 3D volume in accordance with at least one embodiment of the present invention. In at least one embodiment, method 500 comprises block 510, performing one or more C-arm sweeps to collect one or more uncalibrated fluoroscopic images. Block 512 comprises collecting one or more collaborated images (uncalibrated X-ray or fluoroscopic images for example) which, in one embodiment, are transmitted across a local network 514. In one embodiment, method 500 further comprises block 516, calibrating one or more images (calibrated X-ray or fluoroscopic image for example); block 518, computing patient to transmitter transform for the uncalibrated fluoroscopic images; and block 520, forming reconstructing volume for the one or more uncalibrated fluoroscopic images.

The calibrated images, the patient to transmit transform, and the reconstructed volume, are then, in block 522, transmitted across a local area network, 514. Block 524 comprises combining the calibrated images, patient transmitter transform and reconstructed volume forming one or more images. Block 526 comprises displaying the one or more images.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for conducting X-ray image reconstruction comprising:
   collecting at least one uncalibrated image;
   calibrating said at least one uncalibrated image, forming at least one calibrated image; and
   computing a patient to transmitter transform using said at least one uncalibrated image;
   wherein data from transmitter is to determine a position of detector with respect to the patient provided to a tracker module.

2. The method of claim 1 wherein calibrating said at least one uncalibrated comprises locating at least one artifact.

3. The method of claim 1 comprising displaying said at least one image.

4. The method of claim 1 comprising forming a reconstructed volume.

5. The method of claim 4 comprising forming said reconstructed volume using said at least one uncalibrated image.

6. The method of claim 5 comprising combining at least two of said at least one calibrated image, said patient to transmitter transform and said reconstructed volume.

7. A method for reducing metal artifacts in 3D X-ray reconstruction comprising:
- collecting at least one uncalibrated image;
- calibrating said at least one uncalibrated image forming at least one calibrated image;
- computing a patient to transmitter transform using at least said at least one calibrated image;
- forming a reconstructed volume using at least said patient to transmitter transform;
- combimng at least two of said at least one calibrated image, said patient to transmitter transform and said reconstructed volume forming at least one display image; and
- displaying said at least one display image.

8. The method of claim 7 wherein said at least one uncalibrated image comprises at least one uncalibrated fluoroscopic image and said at least one calibrated image comprises at least one calibrated fluoroscopic image.

9. The method of claim 7 wherein calibrating said at least one uncalibrated image comprises performing at least one C-arm sweep.

10. The method of claim 7 wherein calibrating said at least one uncalibrated image comprises locating at least one artifact.

11. The method of claim 7 comprising transmiffing said at least one uncalibrated image across at least one local network.

12. The method of claim 7 wherein calibrating said at least one uncalibrated image comprises removing at least one marker.

13. The method of claim 7 wherein forming said reconstructed volume comprises rotating at least one fluoroscopic image, undoing any C-arm seffings.

14. The method of claim 13 comprising inverting an intensity of said at least one rotated fluoroscopic image.

15. The method of claim 14 comprising filtering said at least one inverted fluoroscopic image for apriori spatially known metal artifacts.

16. The method of claim 15 comprising back projecting at least one filtered fluoroscopic image to form said reconstructed volume.

17. An apparatus for reducing metal artifacts in image reconstruction, comprising:
- a first module adapted to collect at least one uncalibrated image; and
- a second module adapted to calibrate said at least one uncalibrated image, forming at least one calibrated image;
- wherein a patient to transmitter transform is computed using said at least one uncalibrated image;
- wherein data from transmitter is to determine a position of detector with respect to the patient provided to a tracker module.

18. The apparatus of claim 17 comprising a display device adapted to display at least one image having reduced metal artifacts.

* * * * *